United States Patent [19]

Bunnell et al.

[11] Patent Number: 6,020,487
[45] Date of Patent: Feb. 1, 2000

[54] INTERMEDIATES AND PROCESS FOR PREPARING OLANZAPINE

[75] Inventors: Charles Arthur Bunnell, Lafayette; Samuel Dean Larsen, West Lafayette, both of Ind.; John Richard Nichols, Merseyside, United Kingdom; Susan Marie Reutzel, Indianapolis; Gregory Alan Stephenson, Fishers, both of Ind.

[73] Assignee: Eli Lilly and Company, Indianapolis, Ind.

[21] Appl. No.: 08/935,884

[22] Filed: Sep. 23, 1997

Related U.S. Application Data

[60] Provisional application No. 60/026,487, Sep. 23, 1996.

[51] Int. Cl.[7] .................. C07D 495/04; C07D 243/10
[52] U.S. Cl. ........................................... 540/557
[58] Field of Search ............................. 540/557

[56] References Cited

U.S. PATENT DOCUMENTS

| | | | |
|---|---|---|---|
| 5,229,382 | 7/1993 | Chakrabarti et al. | 514/220 |
| 5,302,716 | 4/1994 | Berger et al. | 540/519 |
| 5,550,231 | 8/1996 | Amos et al. | 540/205 |
| 5,602,124 | 2/1997 | Tehim et al. | 514/220 |
| 5,631,250 | 5/1997 | Bunnell et al. | 514/220 |
| 5,637,584 | 6/1997 | Larsen | 514/220 |

FOREIGN PATENT DOCUMENTS

| | | |
|---|---|---|
| 0 369 686 | 5/1990 | European Pat. Off. . |
| 0 582 368 | 2/1994 | European Pat. Off. . |
| 0 733 635 | 9/1996 | European Pat. Off. . |

OTHER PUBLICATIONS

Hampel et al., *Glossary of Chemical Terms*, New York, Van Nostrand Reinhold Company (1982) pp. 148–149.

*Primary Examiner*—Richard L. Raymond
*Assistant Examiner*—Brenda Coleman
*Attorney, Agent, or Firm*—Arleen Palmberg; MaCharri Vorndran-Jones

[57] ABSTRACT

The present invention provides a process for preparing olanzapine and intermediates therefor.

12 Claims, No Drawings

INTERMEDIATES AND PROCESS FOR PREPARING OLANZAPINE

This application claims the benefit of U.S. Provisional Application No. 60/026,487, filed Sep. 23, 1996.

FIELD OF THE INVENTION

This invention relates to a process for preparing 2-methyl-4-(4-methyl-1-piperazinyl)-10H-thieno[2,3-b][1,5]benzodiazepine (referred to herein as "olanzapine"), and to certain dihydrate intermediates.

BACKGROUND OF THE INVENTION

Olanzapine is useful for treating psychotic patients and is currently being investigated for such use. Applicants have discovered that Form II olanzapine is the most stable anhydrous form of olanzapine, providing a stable anhydrous formulation with pharmaceutically desired characteristics, (See European Patent Specification No. 733,635). Careful preparation and controlled conditions are necessary to assure substantially pure Form II olanzapine product (hereinafter referred to as "Form II"); however, Applicants have discovered a process for preparing the desired Form II using a dihydrate olanzapine intermediate under aqueous conditions. In certain situations, Form II which has been prepared from an aqueous solvent may be particularly advantageous. Such Form II material prepared from an aqueous solvent provides assurance that the Form II material is free of substantially all organic solvent residues. This process can provide an especially ecologically desirable method for providing the desired Form II.

SUMMARY OF THE INVENTION

The presently claimed invention provides dihydrate olanzapine which is especially useful as an intermediate for the preparation of Form II olanzapine. The crystalline form may be particularly advantageous.

An especially preferred dihydrate is the stable crystalline Dihydrate D olanzapine polymorph (herein referred to as "Dihydrate D") having a typical x-ray powder diffraction pattern as represented by the following interplanar spacings (d) as set forth in Table 1:

TABLE 1

| d |
|---|
| 9.4511 |
| 7.7098 |
| 7.4482 |
| 6.9807 |
| 6.5252 |
| 5.7076 |
| 5.5539 |
| 5.223 |
| 4.9803 |
| 4.8908 |
| 4.784 |
| 4.6947 |
| 4.4271 |
| 4.3956 |
| 4.3492 |
| 4.2834 |
| 4.1156 |
| 3.7837 |
| 3.7118 |
| 3.5757 |
| 3.482 |
| 3.3758 |

TABLE 1-continued

| d |
|---|
| 3.3274 |
| 3.2413 |
| 3.1879 |
| 3.135 |
| 3.0979 |
| 3.016 |
| 2.9637 |
| 2.907 |
| 2.8256 |
| 2.7914 |
| 2.7317 |
| 2.6732 |
| 2.5863 |

Another especially preferred dehydrate intermediate is the crystalline Dihydrate B olanzapine polymorph (herein referred to as "Dihydrate B") having a typical x-ray powder diffraction pattern as represented by the following interplanar spacings (d) as set forth in Table 2:

TABLE 2

| d |
|---|
| 9.9045 |
| 6.9985 |
| 6.763 |
| 6.4079 |
| 6.1548 |
| 6.0611 |
| 5.8933 |
| 5.6987 |
| 5.4395 |
| 5.1983 |
| 5.0843 |
| 4.9478 |
| 4.7941 |
| 4.696 |
| 4.5272 |
| 4.4351 |
| 4.3474 |
| 4.2657 |
| 4.1954 |
| 4.0555 |
| 3.9903 |
| 3.9244 |
| 3.8561 |
| 3.8137 |
| 3.7671 |
| 3.6989 |
| 3.6527 |
| 3.5665 |
| 3.4879 |
| 3.3911 |
| 3.3289 |
| 3.2316 |
| 3.1982 |
| 3.1393 |
| 3.0824 |
| 2.9899 |
| 2.9484 |
| 2.9081 |
| 2.8551 |
| 2.8324 |
| 2.751 |
| 2.7323 |
| 2.6787 |
| 2.6424 |
| 2.5937 |

Another preferred dehydrate intermediate is the crystalline Dihydrate E olanzapine polymorph (herein referred to as "Dihydrate E") having a typical x-ray powder diffraction pattern as represented by the following interplanar spacings (d) as set forth in Table 3:

TABLE 3

| d |
|---|
| 9.8710 |
| 9.5514 |
| 6.9575 |
| 6.1410 |
| 6.0644 |
| 5.9896 |
| 5.8774 |
| 4.7721 |
| 4.6673 |
| 4.5171 |
| 4.4193 |
| 4.3540 |
| 4.2539 |
| 4.2369 |
| 4.0537 |
| 4.0129 |
| 3.8555 |
| 3.7974 |
| 3.6846 |
| 3.5541 |
| 3.4844 |
| 3.4740 |
| 3.4637 |
| 3.3771 |
| 3.1245 |
| 2.9403 |

The x-ray powder diffraction patterns set forth herein were obtained with a copper k of wavelength=1.541 Å. The interplanar spacings in the column marked "d" are reported in Angstroms. The detector was a Kevex silicon lithium solid state detector.

The presently claimed invention further provides a process for preparing Form II olanzapine comprising drying an olanzapine dihydrate, for instance, in a vacuum oven, at about 40° C. to about 70° C. until the desired Form II is formed.

DETAILED DESCRIPTION OF THE INVENTION

Applicants have discovered that 2-methyl-4-(4-methyl-1-piperazinyl)-10H-thieno[2,3-b][1,5]benzodiazepine, which is a compound of Formula (I):

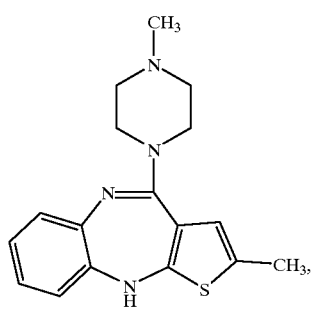

(I)

exists as two different anhydrous forms which are distinguishable by x-ray powder diffractometry. The most stable anhydrous form has been designated Form II. Though Form II must be prepared using carefully controlled conditions, Applicants have discovered that an olanzapine dihydrate can be used for the preparation of Form II. U.S. Pat. No. 5,229,382 is hereby incorporated by reference in its entirety.

The polymorph obtainable by the process taught in the '382 patent is an anhydrate form which is not as desirable for pharmaceutical formulations as Form II. The anhydrate obtainable by the process of the '382 patent will be designated as Form I and has a typical x-ray powder diffraction pattern substantially as follows, obtained using a Siemens D5000 x-ray powder diffractometer, wherein d represents the interplanar spacing:

d 9.9463
8.5579
8.2445
6.8862
6.3787
6.2439
5.5895
5.3055
4.9815
4.8333
4.7255
4.6286
4.533
4.4624
4.2915
4.2346
4.0855
3.8254
3.7489
3.6983
3.5817
3.5064
3.3392
3.2806
3.2138
3.1118
3.0507
2.948
2.8172
2.7589
2.6597
2.6336
2.5956

A typical example of an x-ray diffraction pattern for Form I is as follows wherein d represents the interplanar spacing and $I/I_1$ represents the typical relative intensities:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |

-continued

| d | I/I$_1$ |
|---|---|
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns herein were obtained with a copper K$_a$ of wavelength l=1.541 Å. The interplanar spacings in the column marked "d" are in Angstroms. The typical relative intensities are in the column marked "I/I$_1$".

As used herein "substantially pure" refers to Form II associated with less than about 20% solvated and less than about 5% Form I, preferably less than about 5% solvated and/or Form I, and more preferably less than about 1% solvated and Form I. Further, "substantially pure" Form II will contain less than about 0.5% related substances, wherein "related substances" refers to undesired chemical impurities or residual organic solvent.

Advantageously, the polymorph prepared using the process and intermediates of this invention will be free from chemical solvates, for instance existing as the substantially pure Form II.

It is especially preferred that the dihydrate intermediate is selected from the group consisting of pure Dihydrate B, Dihydrate D, and Dihydrate E. As used herein the term "pure" refers to less than about 20% undesired Dihydrate. More preferredly, the term refers to less than about 10% undesired dihydrate. It may be especially preferred that "pure" refers to less than about 5% undesired dihydrate.

A typical example of an x-ray diffraction pattern for Dihydrate D is as follows wherein d represents the interplanar spacing and I/I$_1$ represents the typical relative intensities:

| d | I/I$_1$ |
|---|---|
| 9.4511 | 100.00 |
| 7.7098 | 14.23 |
| 7.4482 | 22.43 |
| 6.9807 | 5.73 |
| 6.5252 | 5.45 |
| 5.7076 | 4.24 |
| 5.5539 | 1.60 |
| 5.223 | 62.98 |
| 4.9803 | 22.21 |
| 4.8908 | 15.03 |
| 4.784 | 27.81 |
| 4.6947 | 5.15 |
| 4.4271 | 13.00 |
| 4.3956 | 16.63 |
| 4.3492 | 34.43 |

-continued

| d | I/I$_1$ |
|---|---|
| 4.2834 | 51.38 |
| 4.1156 | 18.32 |
| 3.7837 | 5.30 |
| 3.7118 | 1.56 |
| 3.5757 | 0.71 |
| 3.482 | 9.39 |
| 3.3758 | 24.87 |
| 3.3274 | 13.49 |
| 3.2413 | 5.97 |
| 3.1879 | 1.04 |
| 3.135 | 3.18 |
| 3.0979 | 1.43 |
| 3.016 | 1.95 |
| 2.9637 | 0.48 |
| 2.907 | 2.42 |
| 2.8256 | 7.46 |
| 2.7914 | 3.61 |
| 2.7317 | 1.47 |
| 2.6732 | 5.19 |
| 2.5863 | 10.62 |

The x-ray powder diffraction patterns herein were obtained with a copper K$_a$ of wavelength l=1.541 Å. The interplanar spacings in the column marked "d" are in Angstroms. The typical relative intensities are in the column marked "I/I$_1$".

A typical example of an x-ray diffraction pattern for the Dihydrate B polymorph is as follows wherein d represents the interplanar spacing and I/I$_1$ represents the typical relative intensities:

| d | I/I$_1$ |
|---|---|
| 9.9045 | 100.00 |
| 6.9985 | 0.39 |
| 6.763 | 0.17 |
| 6.4079 | 0.13 |
| 6.1548 | 0.85 |
| 6.0611 | 0.99 |
| 5.8933 | 0.35 |
| 5.6987 | 0.12 |
| 5.4395 | 1.30 |
| 5.1983 | 0.67 |
| 5.0843 | 0.24 |
| 4.9478 | 0.34 |
| 4.7941 | 6.53 |
| 4.696 | 1.26 |
| 4.5272 | 2.65 |
| 4.4351 | 2.18 |
| 4.3474 | 1.85 |
| 4.2657 | 0.49 |
| 4.1954 | 0.69 |
| 4.0555 | 0.42 |
| 3.9903 | 0.89 |
| 3.9244 | 1.52 |
| 3.8561 | 0.99 |
| 3.8137 | 1.44 |
| 3.7671 | 0.92 |
| 3.6989 | 1.78 |
| 3.6527 | 0.60 |
| 3.5665 | 0.34 |
| 3.4879 | 1.41 |
| 3.3911 | 0.27 |
| 3.3289 | 0.20 |
| 3.2316 | 0.31 |
| 3.1982 | 0.19 |
| 3.1393 | 0.35 |
| 3.0824 | 0.18 |
| 2.9899 | 0.26 |
| 2.9484 | 0.38 |
| 2.9081 | 0.29 |
| 2.8551 | 0.37 |

-continued

| d | I/I$_1$ |
|---|---|
| 2.8324 | 0.49 |
| 2.751 | 0.37 |
| 2.7323 | 0.64 |
| 2.6787 | 0.23 |
| 2.6424 | 0.38 |
| 2.5937 | 0.21 |

A typical example of an x-ray diffraction pattern for Dihydrate E is as follows wherein d represents the interplanar spacing and I/I$_1$ represents the typical relative intensities:

| d | I/I$_1$ |
|---|---|
| 9.9178 | 100.00 |
| 9.6046 | 16.75 |
| 7.0163 | 2.44 |
| 6.1987 | 8.78 |
| 6.0971 | 10.62 |
| 5.9179 | 1.73 |
| 4.8087 | 50.14 |
| 4.714 | 10.24 |
| 4.5335 | 14.20 |
| 4.4531 | 7.80 |
| 4.3648 | 3.04 |
| 4.276 | 4.50 |
| 4.0486 | 2.76 |
| 3.8717 | 5.09 |
| 3.8292 | 13.39 |
| 3.7053 | 17.24 |
| 3.5827 | 4.82 |
| 3.4935 | 13.22 |
| 3.3982 | 2.01 |
| 3.3294 | 1.30 |
| 3.2026 | 0.98 |
| 3.145 | 2.66 |
| 3.1225 | 1.63 |
| 3.088 | 2.11 |
| 2.9614 | 2.49 |
| 2.9014 | 1.03 |
| 2.8695 | 2.06 |
| 2.8359 | 1.63 |
| 2.7647 | 1.95 |
| 2.7582 | 1.68 |
| 2.7496 | 1.84 |
| 2.7421 | 1.03 |
| 2.7347 | 1.36 |
| 2.6427 | 2.01 |

The x-ray powder diffraction patterns herein were obtained with a copper K$_a$ of wavelength l=1.541 Å. The interplanar spacings in the column marked "d" are in Angstroms. The typical relative intensities are in the column marked "I/I$_1$".

A typical example of an x-ray diffraction pattern for the anhydrous Form II polymorph is as follows wherein d represents the interplanar spacing and I/I$_1$ represents the typical relative intensities:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |

-continued

| d | I/I$_1$ |
|---|---|
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

The compounds and processes of the present invention are useful for preparing compounds having beneficial central nervous system activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of this invention include the following:

A) An intermediate dihydrate which is the Dihydrate D polymorph of olanzapine;

B) A compound which is the substantially pure Dihydrate D polymorph;

C) An intermediate dihydrate which is the Dihydrate B polymorph of olanzapine;

D) An intermediate dihydrate which is the Dihydrate E polymorph of olanzapine;

E) Process for preparing Form II comprising drying an olanzapine dihydrate in a vacuum oven at about 50° C.;

F) Form II prepared using a dihydrate is used for treating a condition selected from the group consisting of a psychosis, schizophrenia, a schizophreniform disorder, mild anxiety, and acute mania;

G) A formulation comprising Form II and substantially pure Dihydrate D; and

H) A formulation comprising Form II and substantially pure Dihydrate B.

The starting materials for the present invention can be prepared by a variety of procedures well known to those of ordinary skill in the art. The material to be employed as starting materials in the process of this invention can be prepared by the general procedure taught by Chakrabarti in U.S. Pat. No. 5,229,382 ('382), herein incorporated by reference in its entirety.

The Dihydrate D is prepared by extensive stirring of technical olanzapine, which may be prepared as described by Preparation 1, under aqueous conditions. The term "aqueous conditions" refers to an aqueous solvent which may be either water or a solvent mixture comprising water and an organic solvent which is sufficiently water miscible to allow the required stoichiometric quantity of water to be present in the solvent mixture. If a solvent mixture is utilized, then the organic solvent must be removed, leaving behind the water, and/or replaced with water. The term "extensive stirring" shall be from about one (1) hour to about six (6) days; however, the artisan will appreciate that the time will vary with the reaction conditions such as temperature, pressure, and solvent. It may be preferred that extensive stirring refers to at least four (4) hours. It is preferred that the aqueous conditions include an aqueous solvent.

The completion of the reaction may be monitored using x-ray powder diffraction and other such methods familiar to the skilled artisan. Several such techniques are described below.

Compound characterization methods include, for example, x-ray powder pattern analysis, thermogravimetric analysis (TGA), differential scanning calorimetery (DSC), titrametric analysis for water, and $H_1$-NMR analysis for solvent content.

The dihyrates described herein are true dehydrates having two water molecules per drug molecule, wherein the water molecules are incorporated into the crystalline lattice of the dihydrate compound.

The following examples are provided for purposes of illustration and are not to be construed as limiting the scope of the claimed invention.

PREPARATION 1

Technical Grade Olanzapine

Intermediate 1

In a suitable three flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.
A sub-surface nitrogen sparge line was added to remove the ammonia formed during the reaction. The reaction was heated to 120° C. and maintained at that temperature throughout the duration of the reaction. The reactions were followed by HPLC until 5% of the intermediate 1 was left unreacted. After the reaction was complete, the mixture was allowed to cool slowly to 20° C. (about 2 hours). The reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.
Yield: 76.7%; Potency: 98.1%

EXAMPLE 1

Dihydrate D

A 100 g sample of technical grade olanzapine (see Preparation 1) was suspended in water (500 mL). The mixture was stirred at about 25° C. for about 5 days. The product was isolated using vacuum filtration. The product was identified as Dihydrate D olanzapine using x-ray powder analysis. Yield: 100 g. TGA mass loss was 10.2%.

EXAMPLE 2

Dihydrate E

A 0.5 g sample of technical grade olanzapine was suspended in ethyl acetate (10 mL) and toluene (0.6 mL). The mixture was heated to 80° C. until all the solids dissolved. The solution was cooled to 60° C. and water (1 mL) was added slowly. As the solution cooled to room temperature, a crystal slurry formed. The product was isolated using vacuum filtration and dried under ambient conditions. The product was identified as Dihydrate E using x-ray powder analysis and solid state $^{13}C$ NMR. TGA mass loss was 10.5%. Yield: 0.3 g.

EXAMPLE 3

Dihydrate B

A 10 g sample of technical grade olanzapine was suspended in water (88 mL). The mixture was stirred at about 25° C. for 6 hours. The product was isolated using vacuum filtration. The product was identified as Dihydrate B olanzapine using x-ray powder analysis. Yield: 10.86 g.

EXAMPLE 4

Form II

The Dihydrate D of olanzapine, prepared as described by Example 1, is dried in a vacuum oven at about 50° C. under about 100 to 300 mm vacuum for a period of about 27 hours. The resulting material is identified using x-ray powder analysis and identified as Form II.

EXAMPLE 5

The Dihydrate B of olanzapine, is dried in a vacuum oven at about 50° C. under about 100 to 300 mm vacuum for a period of about 30 hours. The resulting material is identified using x-ray powder analysis and identified as Form II.

EXAMPLE 6

The Dihydrate E of olanzapine, is dried in a vacuum oven at about 50° C. under about 100 to 300 mm vacuum for a period of about 30 hours. The resulting material is identified using x-ray powder analysis and identified as Form II.

We claim:

1. An olanzapine dihydrate selected from Dihydrate B and Dihydrate E.

2. A dihydrate of claim 1 which is crystalline Dihydrate B and which has a typical X-ray powder diffraction pattern with the following interplanar spacings (d) in Angstroms:

| d |
|---|
| 9.9045 |
| 6.9985 |
| 6.7630 |
| 6.4079 |
| 6.1548 |
| 6.0611 |
| 5.8933 |
| 5.6987 |
| 5.4395 |
| 5.1983 |
| 5.0843 |
| 4.9478 |
| 4.7941 |
| 4.6960 |
| 4.5272 |
| 4.4351 |
| 4.3474 |
| 4.2657 |
| 4.1954 |
| 4.0555 |
| 3.9903 |
| 3.9244 |
| 3.8561 |
| 3.8137 |
| 3.7671 |
| 3.6989 |
| 3.6527 |
| 3.5665 |
| 3.4879 |
| 3.3911 |
| 3.3289 |
| 3.2316 |
| 3.1982 |
| 3.1393 |
| 3.0824 |
| 2.9899 |
| 2.9484 |
| 2.9081 |
| 2.8551 |
| 2.8324 |
| 2.7510 |
| 2.7323 |
| 2.6787 |
| 2.6424 |
| 2.5937. |

3. A Dihydrate B of claim 2 wherein the diffraction pattern has the following typical relative intensity ($I/I_1$) pattern:

| d | $I/I_1$ |
|---|---|
| 9.9045 | 100.00 |
| 6.9985 | 0.39 |
| 6.7630 | 0.17 |
| 6.4079 | 0.13 |
| 6.1548 | 0.85 |
| 6.0611 | 0.99 |
| 5.8933 | 0.35 |
| 5.6987 | 0.12 |
| 5.4395 | 1.30 |
| 5.1983 | 0.67 |
| 5.0843 | 0.24 |
| 4.9478 | 0.34 |
| 4.7941 | 6.53 |
| 4.6960 | 1.26 |
| 4.5272 | 2.65 |
| 4.4351 | 2.18 |
| 4.3474 | 1.85 |
| 4.2657 | 0.49 |
| 4.1954 | 0.69 |
| 4.0555 | 0.42 |
| 3.9903 | 0.89 |
| 3.9244 | 1.52 |
| 3.8561 | 0.99 |
| 3.8137 | 1.44 |
| 3.7671 | 0.92 |
| 3.6989 | 1.78 |
| 3.6527 | 0.60 |
| 3.5665 | 0.34 |
| 3.4879 | 1.41 |
| 3.3911 | 0.27 |
| 3.3289 | 0.20 |
| 3.2316 | 0.31 |
| 3.1982 | 0.19 |
| 3.1393 | 0.35 |
| 3.0824 | 0.18 |
| 2.9899 | 0.26 |
| 2.9484 | 0.38 |
| 2.9081 | 0.29 |
| 2.8551 | 0.37 |
| 2.8324 | 0.49 |
| 2.7510 | 0.37 |
| 2.7323 | 0.64 |
| 2.6787 | 0.23 |
| 2.6424 | 0.38 |
| 2.5937 | 0.21 |

4. A Dihydrate B of claim 3 in substantially pure form.

5. A dihydrate of claim 1 which is crystalline Dihydrate E and which has a typical X-ray powder diffraction pattern with the following interplanar spacings (d) in Angstroms:

| d |
|---|
| 9.8710 |
| 9.5514 |
| 6.9575 |
| 6.1410 |
| 6.0644 |
| 5.9896 |
| 5.8774 |
| 4.7721 |
| 4.6673 |
| 4.5171 |
| 4.4193 |
| 4.3540 |
| 4.2539 |
| 4.2369 |
| 4.0537 |
| 4.0129 |
| 3.8555 |
| 3.7974 |
| 3.6846 |
| 3.5541 |
| 3.4844 |
| 3.4740 |
| 3.4637 |
| 3.3771 |
| 3.1245 |
| 2.9403. |

6. A Dihydrate E of claim 5 wherein the diffraction pattern has the following typical relative intensity pattern ($I/I_1$):

| d | I/I₁ |
|---|---|
| 9.917 | 100.00 |
| 9.6046 | 16.75 |
| 7.0163 | 2.44 |
| 6.1987 | 8.78 |
| 6.0971 | 10.62 |
| 5.9179 | 1.73 |
| 4.8087 | 50.14 |
| 4.7140 | 10.24 |
| 4.5335 | 14.20 |
| 4.4531 | 7.80 |
| 4.3648 | 3.04 |
| 4.2760 | 4.50 |
| 4.0486 | 2.76 |
| 3.8717 | 5.09 |
| 3.8292 | 13.39 |
| 3.7053 | 17.24 |
| 3.5827 | 4.82 |
| 3.4935 | 13.22 |
| 3.3982 | 2.01 |
| 3.3294 | 1.30 |
| 3.2026 | 0.98 |
| 3.1450 | 2.66 |
| 3.1225 | 1.63 |
| 3.0880 | 2.11 |
| 2.9614 | 2.49 |
| 2.9014 | 1.03 |
| 2.8695 | 2.06 |
| 2.8359 | 1.63 |
| 2.7647 | 1.95 |
| 2.7582 | 1.68 |
| 2.7496 | 1.84 |
| 2.7421 | 1.03 |
| 2.7347 | 1.36 |
| 2.6427 | 2.01 |

7. A Dihydrate E of claim 6 in substantially pure form.

8. A process for preparing substantially pure Form II olanzapine comprising preparing an olanzapine dihydrate selected from Dihydrate B, Dihydrate D and Dihydrate E and drying it until the Form II is prepared.

9. A process of claim 8 wherein the dihydrate is dried in a vacuum oven at about 40° C. to about 70° C.

10. A process of claim 9 wherein the dihydrate is Dihydrate D.

11. A process of claim 9 wherein the dihydrate is Dihydrate B.

12. A process of claim 9 wherein the dihydrate is Dihydrate E.

* * * * *